US008439991B2

(12) United States Patent
Abbott

(10) Patent No.: US 8,439,991 B2
(45) Date of Patent: May 14, 2013

(54) PROCESS FOR THE GENERATION OF A SYNTHESIS GAS

(75) Inventor: Peter Edward James Abbott, Eaglescliffe (GB)

(73) Assignee: Johnson Matthey PLC, London (GB)

(*) Notice: Subject to any disclaimer, the term of this patent is extended or adjusted under 35 U.S.C. 154(b) by 510 days.

(21) Appl. No.: 12/672,038

(22) PCT Filed: Jul. 7, 2008

(86) PCT No.: PCT/GB2008/050544
§ 371 (c)(1),
(2), (4) Date: Feb. 3, 2010

(87) PCT Pub. No.: WO2009/019497
PCT Pub. Date: Feb. 12, 2009

(65) Prior Publication Data
US 2011/0124749 A1    May 26, 2011

(30) Foreign Application Priority Data
Aug. 3, 2007  (GB) .................................. 0715101.2

(51) Int. Cl.
*B01J 8/00* (2006.01)
(52) U.S. Cl.
USPC .............................. 48/61; 48/127.9; 48/197 R
(58) Field of Classification Search ........... 48/61, 127.9, 48/197 R
See application file for complete search history.

(56) References Cited

U.S. PATENT DOCUMENTS

| 2,863,527 | A | * | 12/1958 | Becker et al. ................. 62/625 |
| 3,709,669 | A | * | 1/1973 | Marion et al. ................ 48/215 |
| 3,854,895 | A | * | 12/1974 | Muller ............................ 48/206 |
| 3,993,457 | A | * | 11/1976 | Cahn et al. ................. 48/197 R |
| 4,235,044 | A | * | 11/1980 | Cheung ...................... 48/197 R |
| 4,235,800 | A | | 11/1980 | Pinto |
| 4,330,305 | A | * | 5/1982 | Kuessner et al. .............. 95/161 |
| 4,946,477 | A | | 8/1990 | Perka et al. |
| 5,392,594 | A | | 2/1995 | Moore et al. |
| 5,543,437 | A | * | 8/1996 | Benham et al. .............. 518/700 |
| 2007/0072949 | A1 | | 3/2007 | Ruud et al. |

FOREIGN PATENT DOCUMENTS
EP   0 193 677 A2   9/1986
GB      752000       3/1955

OTHER PUBLICATIONS
Pure & Appl. Chem., vol. 68, No. 1, pp. 149-192, 1996.*

* cited by examiner

Primary Examiner — Robert Havlin
(74) Attorney, Agent, or Firm — RatnerPrestia

(57) ABSTRACT

A process for the generation of a synthesis gas comprising: (a) forming a raw synthesis gas, (b) dividing the raw synthesis gas into first and second streams, (c) subjecting the first stream to the water gas shift reaction to form a shifted gas mixture, (d) cooling the second raw synthesis gas stream and shifted gas mixture to below the dew point to form a dry raw synthesis gas mixture, and a dry shifted gas mixture respectively, (e) feeding the dry raw synthesis gas mixture and a dry shifted gas mixture to a gas-washing unit operating by counter-current solvent flow, such that the solvent flowing through said unit contacts first with the dry raw gas mixture and then the dry shifted gas mixture, and (f) collecting from said gas-washing unit a synthesis gas having a stoichiometry ratio, $R=(H_2-CO_2)/(CO+CO_2)$, in the range 1.4 to 3.3.

23 Claims, 2 Drawing Sheets

PROCESS FOR THE GENERATION OF A SYNTHESIS GAS

CROSS-REFERENCE TO RELATED APPLICATIONS

This application is the U.S. National Phase application of PCT International Application No. PCT/GB2008/050544, filed Jul. 7, 2008, and claims priority of British Patent Application No. 0715101.2, filed Aug. 3, 2007, the disclosures of both of which are incorporated herein by reference in their entirety.

FIELD OF THE INVENTION

This invention relates to a process for generating a synthesis gas from coal, in particular a synthesis gas suitable for the production of methanol, liquid hydrocarbons or synthetic natural gas.

BACKGROUND OF THE INVENTION

Synthesis gas may be generated by a gasification of carbonaceous feedstocks such as coal, petroleum coke or other carbon-rich feedstocks using oxygen or air and steam at elevated temperature and pressure. In particular, coal gasification with oxygen and steam combined with a shift stage in which the raw synthesis gas form the gasification process is subjected to the water-gas shift reaction offers a route to synthesis gases that may be used for methanol production, the production of liquid hydrocarbons by the Fischer-Tropsch process or the production of synthetic natural gas.

SUMMARY OF THE INVENTION

Accordingly, the invention provides a process for the generation of a synthesis gas comprising the steps of:
(a) forming a raw synthesis gas comprising hydrogen and carbon oxides by
  (i) gasification of a carbonaceous feedstock at elevated temperature and pressure, and
  (ii) cooling and washing the resulting gas stream with water,
(b) dividing the raw synthesis gas into first and second streams,
(c) subjecting the first stream of raw synthesis gas, in the presence of steam to the water gas shift reaction to form a shifted gas mixture,
(d) cooling the second raw synthesis gas stream and shifted gas mixture to below the dew point to condense water and separating the resulting condensates therefrom to form a dry raw synthesis gas mixture, and a dry shifted gas mixture respectively,
(e) feeding the dry raw synthesis gas mixture and a dry shifted gas mixture to a gas-washing unit operating by means of counter-current solvent flow, such that the solvent flowing through said unit contacts first with the dry raw gas mixture and then the dry shifted gas mixture, and
(f) collecting from said gas-washing unit a synthesis gas having a stoichiometry ratio, $R=(H_2-CO_2)/(CO+CO_2)$, in the range 1.4 to 3.3.

BRIEF DESCRIPTION OF THE DRAWINGS

The invention is further illustrated by reference to the accompanying drawings in which.

DETAILED DESCRIPTION OF THE INVENTION

Figure 1:
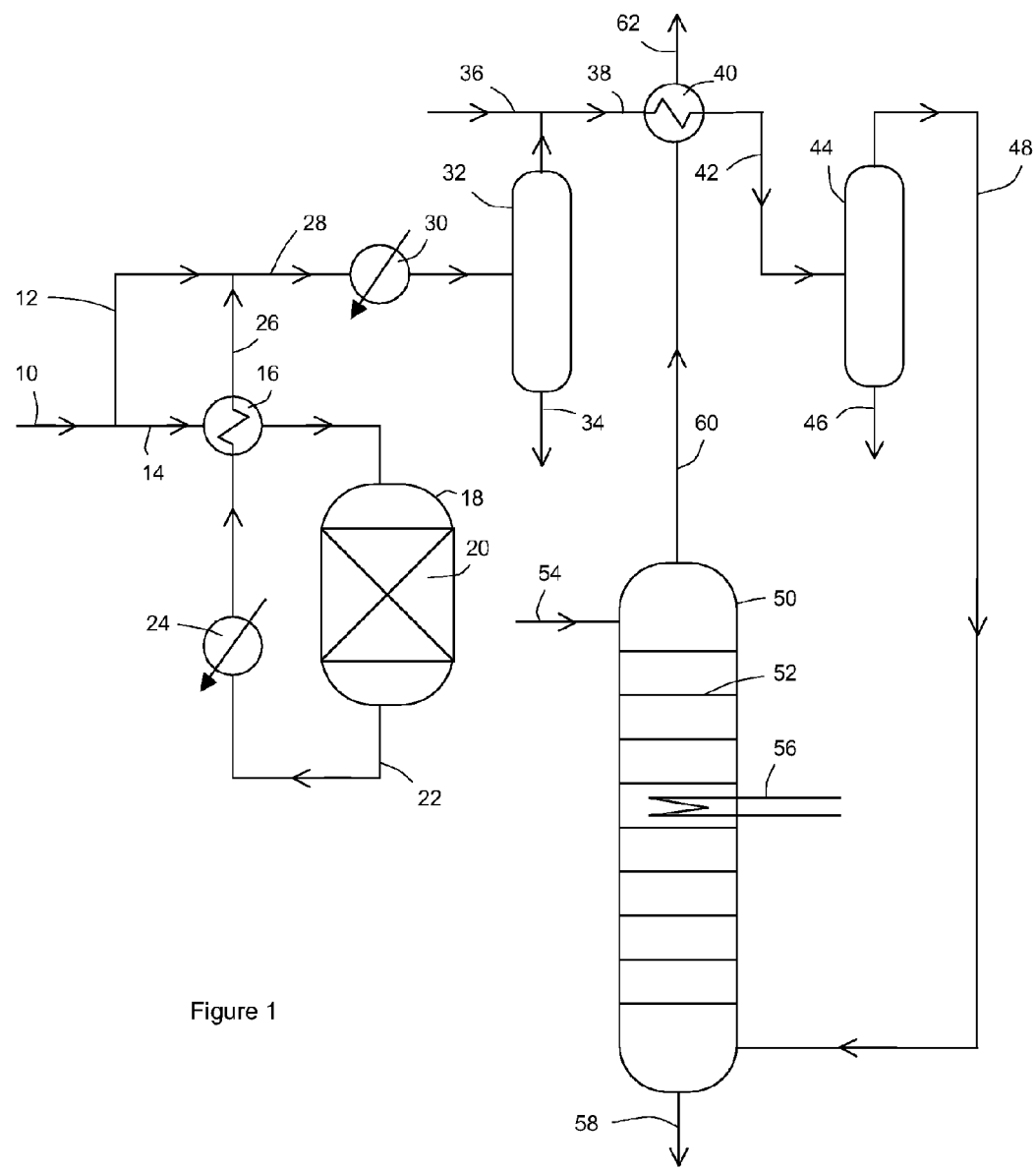
FIG. 1 is a depiction of a comparative process in which a synthesis gas mixture is fed in one step to a gas-washing column utilizing chilled methanol as solvent.

The invention further provides a gas washing unit suitable for removing carbon dioxide from gas mixtures comprising a vessel having a solvent inlet and a solvent outlet, through which a solvent suitable for the dissolution/absorption of carbon dioxide flows, separate first gas mixture and second gas mixture inlets arranged such that the solvent flowing through said unit contacts first with the first gas mixture and then the second gas mixture, and a gas outlet.

In the present invention a raw synthesis gas comprising hydrogen and carbon oxides is produced by gasification of a carbonaceous feedstock at elevated temperature and pressure. Any known gasification technology may be used. The carbonaceous feedstock may be coal, petroleum coke or another carbon-rich feedstock. Preferably the carbonaceous feedstock is a coal. In coal gasification, a coal powder or aqueous slurry may be partially combusted in a gasifier in a non-catalytic process using oxygen or air and in the presence of steam at pressures up to about 75 bar abs and exit temperatures up to about 1450° C., preferably up to about 1400° C., to generate a raw synthesis gas comprising hydrogen and carbon oxides (carbon monoxide and carbon dioxide). The stoichiometry of such raw synthesis gases however is not ideal for the production of methanol or hydrocarbons. In the present invention, the desired stoichiometry ratio, R, which refers to the ratio of molar concentrations of the gas components, $[R=(H_2-CO_2)/(CO+CO_2)]$, is in the range 1.4 to 3.3. R is preferably the range 1.4 to 2.5, more preferably 1.5 to 2.4 for Methanol/FT applications. For generating synthetic natural gas (SNG) the range is preferably in the range 2.8 to 3.3, more preferably 2.9 to 3.2. To achieve this, it is necessary to subject the raw synthesis gas to the water-gas-shift reaction by passing it, in the presence of steam, over a suitable water gas shift catalyst at elevated temperature and pressure. The reaction may be depicted as follows;

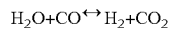

$$H_2O + CO \leftrightarrow H_2 + CO_2$$

Before the raw synthesis gas is subjected to the water gas shift reaction, the gas is cooled and washed, e.g. to remove particulates such as coal ash.

Steam may be added to the raw synthesis gas e.g. by live steam addition or saturation or a combination of these. The steam may be added to the raw synthesis gas before or after it is divided, i.e. steam may be added only to the first stream if desired.

The shift catalyst may be any suitably stable and active water-gas shift catalyst, which may be in a particulate or monolith form. The raw synthesis gas contains sulphur compounds and the water gas shift catalyst must operate in the presence of these compounds. In particular so-called "sour shift" catalysts may be used, in which the active components are metal sulphides. Suitable sour-shift catalysts include supported cobalt-promoted molybdenum catalysts that form molybdenum sulphide in-situ by reaction with hydrogen sulphide present in the raw synthesis gas stream. Alternatively the catalysts may be supplied in a pre-sulphided form. Particularly preferred sour shift catalysts are supported cobalt-molybdate catalysts such as KATALCO K8/11 available from Johnson Matthey PLC, which consists of 3% wt. CoO and 10% wt. $MoO_3$ supported on an inert support containing magnesia and alumina.

In the present invention the raw synthesis gas is divided into first and second streams prior to the water-gas shift stage so that only a portion of the raw synthesis gas is subjected to the water gas shift reaction. The portion that is allowed to by-pass the water gas shift reaction is preferably in the range 10-90% vol of the raw synthesis gas, more preferably 20-80% vol, particularly 25-75% vol. Where the synthesis gas is to be used for methanol production or the synthesis of hydrocarbons using a cobalt-based Fischer-Tropsch catalyst, preferably the portion that is allowed to by-pass the water gas shift reaction is in the range 30-70% vol of the raw synthesis gas, more preferably 40-60% vol, particularly 45-55% vol. For synthesis gas to be used for SNG, the portion, which is allowed to bypass the water gas shift reaction is less, e.g. 10-30% vol, because more water gas shift reaction is required to achieve the higher R value.

The portion of raw synthesis gas that does not by-pass the water gas shift stage is passed at elevated temperature and pressure, preferably temperatures in the range 250 to 500° C. and at the gasifier operating pressure, e.g. up to about 75 bar abs, over the water-gas shift catalyst disposed in a suitable vessel. Preferably the catalyst is a particulate sour shift catalyst. The water-gas shift reaction occurs, consuming carbon monoxide and steam and forming carbon dioxide and hydrogen.

The second stream of raw synthesis gas may, if desired, be subjected to a COS hydrolysis step by passing the raw synthesis gas over a COS hydrolysis catalyst, such as a particulate doped-alumina catalyst. In this step, the COS is hydrolysed by steam to form $H_2S$, which may be easier to remove in the gas-washing unit. In such a COS hydrolysis step, essentially no water-gas shift reaction takes place.

The resulting water gas shifted gas mixture and the by-pass stream of raw synthesis gas are cooled by heat exchange, e.g. with cold water, to below the dew point at which steam condenses. Howsoever the streams are cooled, they are kept separate. The resulting condensates, which comprise water and some contaminants, are separated and may be combined and fed back to the gasifier and/or shift stages.

The resulting dry raw synthesis gas mixture and dry shifted gas mixture may be further cooled and dried, e.g. by means of chilled solvent, and then fed to a gas-washing unit operating by means of counter-current solvent flow. In the gas washing unit, a solvent suitable for the dissolution/absorption of carbon dioxide flows counter-current to gas flowing through the unit and dissolves/absorbs carbon dioxide present in the gas stream. A small quantity of other gas components in the gas stream, particularly carbon monoxide, will also be co-absorbed. Contaminants present in the gas stream that may poison downstream catalysts, e.g. sulphur compounds such as $H_2S$ & COS, may also be removed to differing extents.

Suitable solvents for absorbing $CO_2$ include methanol, particularly where the synthesis gas is to be used to produce methanol, other alcohol or glycol products, such as glycols or polyethylene glycol ethers, and propylene carbonate. Methanol may be used at temperatures in the range −30 to −70° C. and at elevated pressures up to about 75 bar abs. Polyethylene glycol ether solvents may be used at higher temperatures, for example temperatures in the range 20-50° C. The operating pressure in the gas-washing unit may be similar to that of the gasifier, e.g. up to about 75 bar abs.

The $CO_2$-laden solvent is collected from the unit and sent for re-generation, e.g. by heating or reducing the pressure to evolve the $CO_2$, followed by cooling and pressurisation of the solvent to the unit operating pressure and temperature. The regeneration may be carried out in one or more columns, according to design requirements. For instance, a multiple regeneration column layout may be employed if there is a need to recover $CO_2$ and a stream with a high concentration of sulphur compounds separately. The re-generated solvent may then be fed back to the gas washing unit.

Chilled Methanol-based gas washing units and processes are supplied by Linde AG and Lurgi AG under the name Rectisol®. Polyethylene glycol ether-based gas washing units and processes are supplied by UOP (Selexol®), BASF (Sepasolv®) and Clariant (Genosorb). Due to the high solubility of $CO_2$ in chilled methanol, the amount of circulating solvent in the methanol-based gas-washing unit is low in comparison to the polyethylene glycol ether-based processes. Chilled Methanol may also be more effective in capturing $H_2S$ and COS and other minor contaminants (e.g. HCN and metal carbonyls), which could poison downstream catalysts. Accordingly, methanol is often the preferred solvent where a downstream catalyst is being used.

A gas-washing unit may comprise, for example, a column having a solvent inlet near the top and a solvent outlet near the bottom, down which a solvent suitable for the dissolution/absorption of carbon dioxide flows over one or more perforate trays or packing. The gases passing up through the column contact the solvent and carbon dioxide is dissolved/absorbed. The gases may leave the column near the top via a synthesis gas outlet. The synthesis gas is cold and may be used to cool the feed gases to the gas-washing unit using suitable heat exchange means such as a spiral wound heat exchanger.

In the present invention, the dry raw synthesis gas mixture and dry shifted gas mixture are fed separately to the unit, with the separate feeds arranged such that that the solvent contacts first with the dry raw gas mixture and then the dry shifted gas mixture. Hence in a single column unit, the dry shifted gas mixture may be fed to the column near the bottom of the column and the dry raw synthesis gas mixture fed to an intermediate position above the dry shifted gas mixture inlet. This is in contrast to previous processes, where a synthesis gas mixture is fed to a gas-washing unit so that the solvent contacts the gas mixture in one stage. We have found that by separately feeding the two different gas streams to the unit such that that the solvent contacts first with the dry raw gas mixture and then the dry shifted gas mixture, the efficiency of the process is improved, which offers the potential for smaller sized vessels and an increased potential for methanol or liquid hydrocarbon production. For example, in the column embodiment described above, by feeding only the shifted stream to the base of the column, more $CO_2$ and less CO is absorbed in a given mass of circulating wash solvent. Because less CO is removed from the syngas, more $CO_2$ can be removed to give the required stoichiometric gas composition (R ratio). If more $CO_2$ and less CO is removed, this means that the extra $H_2$ produced is available in the product synthesis gas. Because the methanol synthesis or Fischer-Tropsch synthesis process or SNG production process are constrained by $H_2$ availability, in effect this means that there is more synthesis gas available for methanol, liquid hydrocarbon or SNG synthesis from a given quantity of raw synthesis gas exit the gasifier. In addition, because the partial pressure of $CO_2$ is higher, it is possible to make cost savings in the equipment for the unit such as a reduction in solvent re-circulation rate or, for some solvents, operation at a higher temperature requiring less refrigeration.

The sour shift reactor, bypass and gas-washing stage are operated such that the synthesis gas collected from the gas-washing unit has a stoichiometry ratio, $R=(H_2-CO_2)/(CO+CO_2)$, in the range 1.4 to 3.3. This may be achieved principally by setting the bypass flow around the shift reactor, as this governs the quantity of $CO_2$ formed from CO and subsequently removed in the gas-washing unit.

The synthesis gas generated by the process of the present invention may be used in the production of methanol or for the Fischer-Tropsch Synthesis of liquid hydrocarbons or the production of synthetic natural gas.

Methanol production is generally performed by passing a synthesis gas comprising hydrogen, carbon oxides and any inert gases at an elevated temperature and pressure through one or more beds of a methanol synthesis catalyst, which is often a copper-containing composition. Methanol is generally recovered by cooling the product gas stream to below the dew point of the methanol and separating off the product as a liquid. The process is often operated in a loop: thus the remaining unreacted gas stream is usually recycled to the synthesis reactor as part of the synthesis gas via a circulator. Fresh synthesis gas, termed make-up gas, is added to the recycled unreacted gas to form the synthesis gas stream. A purge stream is taken from the circulating gas stream to avoid the build up of inert gasses. The methanol synthesis may be performed at pressures in the range 40-150, and more conveniently in the range 45-120, bar abs. The temperature of the synthesis catalyst is suitably in the range 160-300° C.; preferably the peak temperature is below 285° C. The synthesis gas preferably enters the catalyst beds at a temperature in the range 200-250° C. and leaves the beds at temperatures preferably in the range 220-260° C. The synthesis catalyst is preferably a copper-based catalyst containing copper and compounds, e.g. oxides of zinc, aluminium, chromium, titanium, zirconium, and/or magnesium. The catalyst may be in the form of pellets, tablets or extrudates. Particularly preferred catalysts are described in U.S. Pat. No. 4,788,175.

The Fischer-Tropsch synthesis converts a mixture of carbon monoxide and hydrogen to hydrocarbons over reduced cobalt- or iron-based catalysts. In this case the $CO_2$, in contrast to methanol synthesis, is not a co-reactant with the CO. Because Fe-based catalysts normally have a significant water gas shift activity, whereas Co-based catalysts do not, it will usually be necessary to extract more $CO_2$ from the synthesis gas feed for Co-based Fischer-Tropsch synthesis as opposed to Fe-based one. The mixture of carbon monoxide and hydrogen fed to the catalyst typically has a hydrogen:carbon monoxide ratio in the range 1.4-2.5:1, depending on application and catalyst type. The reaction may be performed in a continuous or batch process using one or more stirred slurry-phase reactors, bubble-column reactors, loop reactors or fluidised bed reactors. The process may be operated at pressures in the range 0.1-10 Mpa and temperatures in the range 150-350° C. The gas-hourly-space velocity (GHSV) for continuous operation is in the range 100-25000 $hr^{-1}$.

In one process to make synthetic natural gas, the synthesis gas comprising carbon monoxide and carbon dioxide and hydrogen is reacted over a reduced supported nickel-based catalyst in one or more reactors, preferably two or more reactors to form methane and water in a highly exothermic (methanation) reaction. The water and any remaining carbon dioxide may be removed using known techniques. If the feed gas contains carbon oxides and hydrogen in close to stoichiometric ratio (R=3.0), then a high purity methane stream (typically methane >95 vol %) can be produced, which can be used as a Synthetic Natural Gas.

In FIG. 1, a raw synthesis gas 10 comprising hydrogen, steam and carbon oxides, obtained by gasification of coal using oxygen, followed by cooling, washing and admixture with steam, is divided into a bypass stream 12 and shift feed stream 14. The shift feed stream 14 is preheated in heat exchanger 16 and passed to shift converter 18 containing a fixed bed of a particulate sour shift catalyst 20. The water gas shift reaction takes place converting some of the CO present in the raw synthesis gas into $CO_2$. The resulting shifted gas mixture is fed from converter 18 via line 22 to a first heat exchanger 24 where it is cooled and then to the heat exchanger 16 where it is used to heat the feed stream 14. The resulting cooled shifted gas in line 26 is mixed with the by-pass stream 12 of raw synthesis gas and the combined mixture fed via line 28 to heat exchanger 30 where it is cooled to below the dew point to cause water to condense from the gases. The mixture from heat exchanger 30 is passed to a separator 32, which separates the condensate 34. The partially dried gas stream from separator 32 is mixed with methanol fed via line 36 and the mixture fed via line 38 to a heat exchanger 40, e.g. a spiral-wound heat exchanger, where it is further cooled. The cold mixture is passed from exchanger 40 via line 42 to a second separator 44, which separates the methanol and remaining water 46 from the synthesis gas mixture. The resulting dry synthesis gas mixture is passed from the separator 44 via line 48 to near the base of a gas-washing column 50, comprising a plurality of perforate trays 52. Chilled, regenerated methanol is fed to near the top of the column 50 vial line 54 and passes down the column through the perforations in the trays 52. As the methanol passes down the column, it absorbs/dissolves $CO_2$ from the gas stream passing in the opposite direction. Some CO and contaminants are also absorbed. Refrigeration coils 56 are provided in the column to maintain the desired operating temperature. The $CO_2$-laden methanol solvent is recovered from the base of the column via line 58 and sent for regeneration. The $CO_2$-depleted synthesis gas is collected from the top of the column 50 and fed via line 60 to heat exchanger 40 where it is used to cool the methanol/synthesis gas mixture in line 38. The synthesis gas stream having the desired stoichiometry ratio is obtained from the heat exchanger 40 via line 62.

Figure 2:
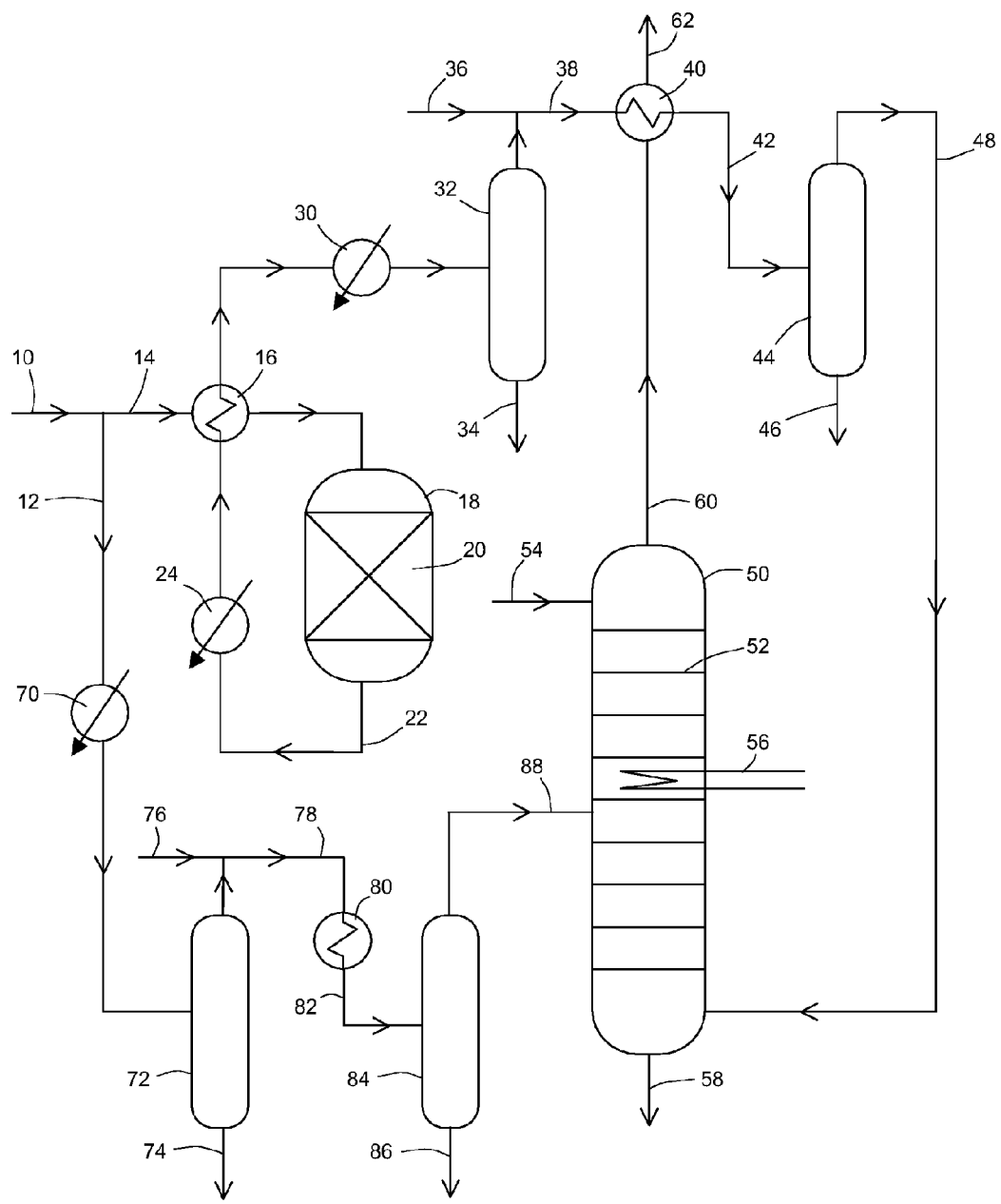
FIG. 2 is a depiction of one embodiment according to the present invention in which a dry raw synthesis gas mixture and a dry shifted gas mixture are fed separately to the unit, with the separate feeds arranged such that that the chilled methanol solvent contacts first with the dry raw gas mixture and then the dry shifted gas mixture.

In FIG. 2 a raw synthesis gas 10 comprising hydrogen, steam and carbon oxides, obtained by gasification of coal using oxygen, followed by cooling, washing and admixture with steam, is divided into a bypass stream 12 and shift feed stream 14. The shift feed stream 14 is pre-heated in heat exchanger 16 and passed to shift converter 18 containing a fixed bed of a particulate sour shift catalyst 20. The water gas shift reaction takes place converting some of the CO present in the raw synthesis gas into $CO_2$. The resulting shifted gas mixture is fed from converter 18 via line 22 to a first heat exchanger 24 where it is cooled and then to the heat exchanger 16 where it is used to head the feed stream 14. The resulting cooled shifted gas in line 26 is fed to heat exchanger 30 where it is cooled to below the dew point to cause water to condense from the gases. The mixture from heat exchanger 30 is passed to a separator 32, which separates the condensate 34. The partially dried gas stream from separator 32 is mixed with methanol fed via line 36 and the mixture fed via line 38 to a heat exchanger 40, e.g. a spiral-wound heat exchanger, where it is further cooled. The cold mixture is passed from exchanger 40 via line 42 to a second separator 44, which separates the methanol and remaining water 46 from the synthesis gas mixture. The resulting dry synthesis gas mixture is passed from the separator 44 via line 48 to near the base of a gas-washing column 50, comprising a plurality of perforate trays 52.

The bypass stream 12 or raw synthesis gas is not mixed with the shifted gas mixture but is instead cooled in heat exchanger 70 where it is cooled to below the dew point to cause water to condense from the gases. The mixture from heat exchanger 70 is passed to a separator 72, which separates the condensate 74. The partially dried gas stream from separator 72 is mixed with methanol fed via line 76 and the mixture fed via line 78 to a heat exchanger 80, e.g. a spiral-wound heat exchanger, where it is further cooled. The cold mixture is passed from exchanger 80 via line 82 to a second separator 84, which separates the methanol and remaining water 86 from the synthesis gas mixture. The resulting dry synthesis gas mixture is passed from the separator 84 via line 88 to the gas-washing column 50 at a position about one-third to about one-half of the effective column height.

Chilled, regenerated methanol is fed to near the top of the column 50 vial line 54 and passes down the column through the perforations in the trays 52. As the methanol passes down the column, it first contacts the dry raw synthesis gas mixture before it contacts with the dry shifted gas mixture passing in the opposite direction. Refrigeration coils 56 are provided in the column to maintain the desired operating temperature. The $CO_2$-laden methanol solvent is recovered from the base of the column via line 58 and sent for regeneration. The combined $CO_2$-depleted synthesis gas is collected from the top of the column 50 and fed via line 60 to heat exchanger 40 where it is used to cool the methanol/synthesis gas mixture in line 38. The synthesis gas in line 60 may also be used to cool the methanol/synthesis gas mixture 78 in heat exchanger 80. The synthesis gas stream having the desired stoichiometry ratio is obtained from the heat exchanger 40 via line 62.

The condensates 34 and 74 may be combined and used to generate steam for e.g. the gasification or shift stages. The methanol/water mixtures 46 and 86 may be combined and fed to methanol purification.

EXAMPLES

The invention is further illustrated by reference to the following calculated examples in accordance with the processes as depicted in FIGS. 1 and 2.

Comparative Example in Accordance with FIG. 1

| | | Stream | | | | | | |
|---|---|---|---|---|---|---|---|---|
| | | 10 | 14 | 12 | 22 | 28 | 54 | 60 | 58 |
| Flow | kgmols/hr | 64722.8 | 35270.1 | 29452.7 | 35270.1 | 64722.8 | 34111.6 | 23334.5 | 44715 |
| Flow | kgs/hr | 1266026 | 689909 | 576117 | 689909 | 1266026 | 1093000 | 249082 | 1551535 |
| Pressure | bara | 63.0 | 63.0 | 63.0 | 62.5 | 62.0 | 60.0 | 58.0 | 60.0 |
| Temp. | deg C. | 240 | 240 | 240 | 421 | 249 | −30 | −30 | −37 |
| Compn | mol frac. | | | | | | | | |
| $H_2$ | | 0.1776 | 0.1776 | 0.1776 | 0.3032 | 0.2460 | 0.0000 | 0.6793 | 0.0015 |
| CO | | 0.1789 | 0.1789 | 0.1789 | 0.0533 | 0.1105 | 0.0000 | 0.2942 | 0.0062 |
| $CO_2$ | | 0.0981 | 0.0981 | 0.0981 | 0.2236 | 0.1665 | 0.0000 | 0.0200 | 0.2274 |
| $N_2$ | | 0.0014 | 0.0014 | 0.0014 | 0.0014 | 0.0014 | 0.0000 | 0.0038 | 0.0000 |
| $CH_4$ | | 0.0004 | 0.0004 | 0.0004 | 0.0004 | 0.0004 | 0.0000 | 0.0010 | 0.0001 |
| $NH_3$ | | 0.0011 | 0.0011 | 0.0011 | 0.0011 | 0.0011 | 0.0000 | 0.0000 | 0.0001 |
| $H_2O$ | | 0.5406 | 0.5406 | 0.5406 | 0.4150 | 0.4722 | 0.0000 | 0.0000 | 0.0000 |
| $H_2S$ | | 0.0012 | 0.0012 | 0.0012 | 0.0013 | 0.0012 | 0.0000 | 0.0000 | 0.0017 |
| COS | | 0.0001 | 0.0001 | 0.0001 | 0.0000 | 0.0001 | 0.0000 | 0.0000 | 0.0001 |
| Ar | | 0.0006 | 0.0006 | 0.0006 | 0.0006 | 0.0006 | 0.0000 | 0.0016 | 0.0000 |
| $CH_3OH$ | | 0.0000 | 0.0000 | 0.0000 | 0.0000 | 0.0000 | 1.0000 | 0.0001 | 0.7628 |

Example 1 in Accordance with FIG. 2

| | | Stream | | | | | | |
|---|---|---|---|---|---|---|---|---|
| | | 10 | 14 | 12 | 22 | 54 | 60 | 58 |
| Flow | kgmols/hr | 64722.8 | 36118.8 | 28604 | 36118.8 | 33081.7 | 23475 | 43664.7 |
| Flow | kgs/hr | 1266026 | 706510 | 559516 | 706510 | 1060000 | 250605 | 1519433 |
| Pressure | bara | 63.0 | 63.0 | 63.0 | 62.5 | 60.0 | 58.0 | 60.0 |
| Temp. | deg C. | 240 | 240 | 240 | 420.8 | −30 | −30 | −37 |
| Compn | mol frac. | | | | | | | |
| $H_2$ | | 0.1776 | 0.1776 | 0.1776 | 0.3031 | 0.0000 | 0.6794 | 0.0018 |
| CO | | 0.1789 | 0.1789 | 0.1789 | 0.0534 | 0.0000 | 0.2942 | 0.0030 |
| $CO_2$ | | 0.0981 | 0.0981 | 0.0981 | 0.2237 | 0.0000 | 0.0200 | 0.2355 |
| $N_2$ | | 0.0014 | 0.0014 | 0.0014 | 0.0014 | 0.0000 | 0.0038 | 0.0000 |
| $CH_4$ | | 0.0004 | 0.0004 | 0.0004 | 0.0004 | 0.0000 | 0.0010 | 0.0001 |
| $NH_3$ | | 0.0011 | 0.0011 | 0.0011 | 0.0011 | 0.0000 | 0.0000 | 0.0001 |
| $H_2O$ | | 0.5406 | 0.5406 | 0.5406 | 0.4150 | 0.0000 | 0.0000 | 0.0000 |
| $H_2S$ | | 0.0012 | 0.0012 | 0.0012 | 0.0013 | 0.0000 | 0.0000 | 0.0018 |
| COS | | 0.0001 | 0.0001 | 0.0001 | 0.0000 | 0.0000 | 0.0000 | 0.0001 |
| Ar | | 0.0006 | 0.0006 | 0.0006 | 0.0006 | 0.0000 | 0.0015 | 0.0000 |
| $CH_3OH$ | | 0.0000 | 0.0000 | 0.0000 | 0.0000 | 1.0000 | 0.0001 | 0.7576 |

The calculations show that there is an increase of synthesis gas flow-rate available from the wash unit of the same composition of approx. 0.6% (due principally to less co-absorption of CO). This is anticipated to be of economic advantage, because it means that all equipment upstream of and including the wash unit, except the Sour Shift vessel, can be made smaller for the same flow of synthesis gas fed downstream (i.e. the gasifier and air separation unit for oxygen production). Alternatively the increased synthesis gas may be translated into increased methanol or liquid hydrocarbon production.

There is also a small saving on the required wash solvent re-circulation rate. An alternate way to reduce operating costs may be to have the same circulation rate, but chill it slightly less.

Whereas the sour shift bypass stream has to be cooled in separate heat exchangers and separately treated to remove its water content, for a large plant, where there is multi-streaming, this may not mean extra equipment items.

The invention claimed is:

1. A process for the generation of a synthesis gas comprising:
    (a) forming a raw synthesis gas comprising hydrogen and carbon oxides by:
        (i) gasification of a carbonaceous feedstock at elevated temperature and pressure, and
        (ii) cooling and washing a resulting gas stream with water;
    (b) dividing the raw synthesis gas into first and second streams;
    (c) subjecting the first raw synthesis gas stream, in the presence of steam, to a water gas shift reaction to form a shifted gas mixture;
    (d) cooling the second raw synthesis gas stream and cooling the shifted gas mixture to below the dew point to condense water and separating resulting condensates therefrom to form, respectively, a dry raw synthesis gas mixture and a dry shifted gas mixture;
    (e) feeding the dry raw synthesis gas mixture and the dry shifted gas mixture to a gas-washing unit operating by a counter-current solvent flow, wherein a solvent flowing through said gas-washing unit contacts first with the dry raw gas mixture and then the dry shifted gas mixture; and
    (f) collecting from said gas-washing unit a synthesis gas having a molar ratio, $R=([H_2]-[CO_2])/([CO]+[CO_2])$, in the range 1.4 to 3.3.

2. A process according to claim 1 where R is in the range 1.4 to 2.5.

3. A process according to claim 1 wherein the carbonaceous feedstock is coal.

4. A process according to claim 1 wherein the gasification is performed with oxygen.

5. A process according to claim 3 wherein the gasification is performed on a coal powder or aqueous slurry of coal in a gasifier using oxygen or air and in the presence of steam at a pressure up to about 75 bar abs and an exit temperature up to about 1450° C.

6. A process according to claim 1 wherein before the raw synthesis gas is subjected to the water gas shift reaction, the gas is combined with steam.

7. A process according to claim 1 wherein the first raw synthesis gas stream comprises between 10% and 90% vol of the raw synthesis gas and the second raw synthesis gas stream between 90% and 10% vol of the raw synthesis gas.

8. A process according to claim 1 wherein the first raw synthesis gas stream is subjected to the water-gas shift reaction in a vessel containing a supported cobalt-promoted molybdenum catalyst.

9. A process according to claim 8 wherein the water gas shift reaction is performed at a temperature in the range of 250 to 500° C.

10. A process according to claim 1 wherein the second raw synthesis gas stream is subjected to a COS hydrolysis step before the water is removed.

11. A process according to claim 1 wherein the solvent used in the gas-washing unit is selected from the group consisting of methanol, alcohols, glycol products and propylene carbonate.

12. A process according to claim 1 wherein the solvent in the gas-washing unit is methanol.

13. A process according to claim 12 wherein the methanol is used in the gas washing unit at temperatures in the range −30 to −70° C. and at elevated pressures up to about 75 bar abs.

14. A process according to claim 1 wherein the solvent in the gas-washing unit is a polyethylene glycol ether.

15. A process according to claim 1 wherein the gas-washing unit comprises a column having a solvent inlet near the top and a solvent outlet near the bottom, down which said solvent suitable for the dissolution/absorption of carbon dioxide flows over one or more perforate trays or packing, separate dry raw synthesis gas mixture and dry shifted gas mixture inlets arranged such that the solvent flowing through said unit contacts first with the dry raw gas mixture and then the dry shifted gas mixture gas, and a synthesis gas outlet.

16. A process according to claim 1 wherein the product synthesis gas is used to cool the feed gases to the gas-washing unit.

17. A process for the production of methanol comprising: forming a synthesis gas having a stoichiometry molar ratio, $R=([H_2]-[CO_2])/([CO]+[CO2])$, in the range 1.4 to 2.5 according to the process of claim 1 and passing said synthesis gas at an elevated temperature and pressure through one or more beds of a methanol synthesis catalyst.

18. A methanol production process according to claim 17, performed at pressures in the range 40-150 bar abs and with a synthesis gas temperature in the range 160-300° C.

19. A methanol production process according to claim 17 wherein the methanol synthesis catalyst is a copper-based catalyst containing copper and one or more oxides of zinc, aluminium, chromium, titanium, zirconium, and magnesium.

20. A process for the synthesis of liquid hydrocarbons comprising: forming a synthesis gas having a molar ratio, $R=([H_2]-[CO_2])/([CO]+[CO_2])$, in the range 1.4 to 2.5 according to the process of claim 1, then, adjusting the hydrogen to carbon monoxide ratio such that the synthesis gas has a hydrogen:carbon monoxide ratio in the range 1.5-2.5:1, and passing said synthesis gas at an elevated temperature and pressure over a cobalt- or iron-based Fischer-Tropsch catalyst in a suitable vessel.

21. A process for the synthesis of liquid hydrocarbons according to claim 20 wherein the reaction is performed at a pressure in the range 0.1-10 Mpa and a temperature in the range 150-350° C.

22. A process for the synthesis of liquid hydrocarbons according to claim 20 wherein the reaction is performed in a continuous or batch process using one or more stirred slurry-phase reactors, bubble-column reactors, loop reactors or fluidised bed reactors.

23. A process for the production of a synthetic natural gas comprising: forming a synthesis gas having a molar ratio, $R=([H_2]-[CO_2])/([CO]+[CO_2])$, in the range 2.8 to 3.3 according to the process of claim 1, and passing said synthesis gas over a supported Ni catalyst in one or more reactors.

* * * * *

UNITED STATES PATENT AND TRADEMARK OFFICE
CERTIFICATE OF CORRECTION

PATENT NO.        : 8,439,991 B2                           Page 1 of 1
APPLICATION NO.   : 12/672038
DATED             : May 14, 2013
INVENTOR(S)       : Peter Edward James Abbott It is certified that error appears in the above-identified patent and that said Letters Patent is hereby corrected as shown below:

In the Claims:

At Column 9, in claim 1, lines 38 through 43 of the Letters Patent,

"(e)   feeding the dry raw synthesis gas mixture and the dry shifted gas mixture to a gas-washing unit operating by a counter-current solvent flow, wherein a solvent flowing through said gas-washing unit contacts first with the dry raw gas mixture and then the dry shifted gas mixture; and" should read -- (e)   feeding the dry raw synthesis gas mixture and the dry shifted gas mixture to a vertically oriented gas-washing unit operating by a counter-current solvent flow, wherein the gas-washing unit comprises separate inlets for the dry shifted gas mixture and the dry raw synthesis gas mixture, wherein the inlet for the dry shifted gas mixture is below the inlet for the dry raw syntheses gas mixture, and wherein a solvent flowing through said gas-washing unit contacts first with the dry raw synthesis gas mixture and then the dry shifted gas mixture; and --

At Column 10, in claim 15, lines 19 through 27 of the Letters Patent,

"A process according to claim 1 wherein the gas-washing unit comprises a column having a solvent inlet near the top and a solvent outlet near the bottom, down which said solvent suitable for the dissolution/absorption of carbon dioxide flows over one or more perforate trays or packing, separate dry raw synthesis gas mixture and dry shifted gas mixture inlets arranged such that the solvent flowing through said unit contacts first with the dry raw gas mixture and then the dry shifted gas mixture gas, and a synthesis gas outlet." should read -- A process according to claim 1 wherein the gas-washing unit comprises a column having a solvent inlet near the top and a solvent outlet near the bottom, down which said solvent suitable for the dissolution/absorption of carbon dioxide flows over one or more perforate trays or packing, and a synthesis gas outlet. --

Signed and Sealed this
Twenty-fourth Day of September, 2013

Teresa Stanek Rea
*Deputy Director of the United States Patent and Trademark Office*